United States Patent [19]

Borzatta

[11] Patent Number: 5,102,928
[45] Date of Patent: Apr. 7, 1992

[54] PIPERIDINE-TRIAZINE COMPOUNDS FOR USE AS STABILIZERS FOR ORGANIC MATERIALS

[75] Inventor: Valerio Borzatta, Bologna, Italy

[73] Assignee: Ciba-Ceigy Corporation, Ardsley, N.Y.

[21] Appl. No.: 630,100

[22] Filed: Dec. 19, 1990

[30] Foreign Application Priority Data

Dec. 28, 1989 [IT] Italy ................... 22866A/89

[51] Int. Cl.⁵ ............... C08K 5/3492; C07D 295/00; C07D /251/68
[52] U.S. Cl. ................................ 524/100; 106/176; 252/475; 252/51.5 R; 540/575; 544/113; 544/198; 544/209; 544/212; 554/5
[58] Field of Search .............. 524/100; 544/198, 209, 544/212, 113; 540/575; 260/398.5; 106/176; 252/47.5, 51.5 R

[56] References Cited

U.S. PATENT DOCUMENTS

| | | | |
|---|---|---|---|
| 4,086,204 | 4/1978 | Cassandrini et al. | 544/207 |
| 4,108,829 | 8/1978 | Cassandrini et al. | 544/219 |
| 4,263,434 | 4/1981 | Cassandrini et al. | 544/198 |
| 4,315,859 | 2/1982 | Nikles | 544/198 |
| 4,331,586 | 5/1982 | Hardy | 544/113 |
| 4,335,242 | 6/1982 | Wiezer et al. | 544/198 |
| 4,433,145 | 2/1984 | Wiezer et al. | 544/198 |
| 4,459,395 | 7/1984 | Cantatore | 544/198 |
| 4,477,615 | 10/1984 | Raspanti et al. | 544/198 |
| 4,843,159 | 6/1989 | Cantatore et al. | 544/198 |
| 4,883,870 | 11/1989 | Cantatore et al. | 524/100 |
| 4,997,938 | 3/1991 | Cantatore et al. | 524/100 |

FOREIGN PATENT DOCUMENTS

| | | |
|---|---|---|
| 0053775 | 6/1982 | European Pat. Off. |
| 117229 | 8/1984 | European Pat. Off. |
| 299925 | 1/1989 | European Pat. Off. |
| 376886 | 7/1990 | European Pat. Off. |
| 63-196654 | 8/1988 | Japan |

OTHER PUBLICATIONS

Chem. Abst. 97, 183468d (1982).
Chem. Abst. 100, 193010t (1984).

*Primary Examiner*—Veronica P. Hoke
*Attorney, Agent, or Firm*—Lurther A. R. Hall

[57] ABSTRACT

The present invention relates to novel piperidine-triazine compounds of the general formula (I)

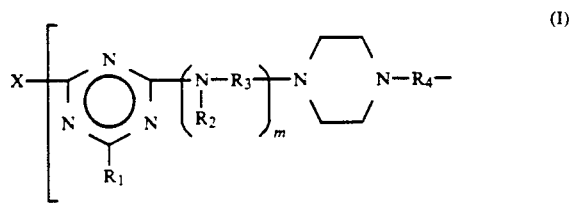

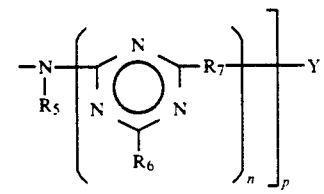

in which $R_1$ and $R_6$ are e.g. isooctylamino or N-(2,2,6,6-tetramethyl-4-piperidyl)-butylamino, $R_2$ and $R_5$ are e.g. 2,2,6,6-tetramethyl-4-piperidyl, $R_3$ and $R_4$ are e.g. alkylene, $R_7$ is e.g. a group

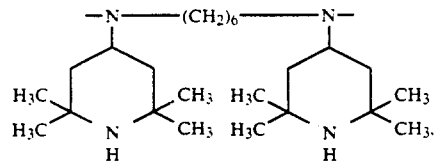

m is zero or 1, n is zero, 1,2,3 or 4, p is 1 to 50, X is e.g. as defined for $R_1$ and Y is e.g. a group

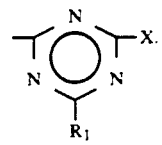

The said compounds are effective as light stabilizers, heat stabilizers and oxidation stabilizers for organic materials.

13 Claims, No Drawings

PIPERIDINE-TRIAZINE COMPOUNDS FOR USE AS STABILIZERS FOR ORGANIC MATERIALS

The present invention relates to novel piperidine-triazine compounds, to their use as light stabilizers, heat stabilizers and oxidation stabilizers for organic materials, in particular synthetic polymers, and to organic materials thus stabilized.

It is known that synthetic polymers undergo a progressive change in physical properties, such as loss of mechanical strength and a colour change, when they are exposed to the action of sunlight or other sources of ultraviolet light in the presence of oxygen.

To delay the detrimental effect of ultraviolet radiation on synthetic polymers, additives having photostabilizing properties are used, such as certain derivatives of benzophenone and benzotriazole, nickel complexes, alkylidenemalonates, cyanoacrylates, aromatic oxamides or sterically hindered amines.

Some triazine oligomers containing 2,2,6,6-tetramethyl-4-piperidyl groups and their use as stabilizers for synthetic polymers have been reported in U.S. Pat. Nos. 4,086,204, 4,315,859, 4,331,586, 4,335,242, 4,459,395 and 4,477,615, in European laid open prints 117,229, 376,886 and 299,925 and in Japanese laid open print Sho 63-196,654.

The present invention relates to novel piperidine-triazine compounds of the general formula (I)

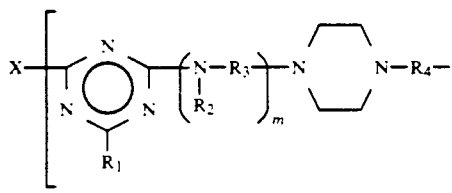

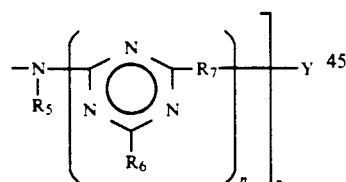
(I)

in which m is zero or 1, n is zero, 1, 2, 3 or 4, $R_1$ and $R_6$ which can be identical or different are a group $-OR_8$, $-SR_8$ or

in which $R_8$ is hydrogen, $C_1$–$C_{18}$alkyl, $C_5$–$C_{12}$cycloalkyl which is unsubstituted or mono-, di- or trisubstituted by $C_1$–$C_4$alkyl, $C_3$–$C_{18}$alkenyl, $C_7$–$C_9$-phenylalkyl which is unsubstituted or mono-, di- or trisubstituted on the phenyl by $C_1$–$C_4$alkyl, phenyl which is unsubstituted or mono-, di- or tri-substituted by $C_1$–$C_4$alkyl or by $C_1$–$C_4$alkoxy, or a group of the formula (II)

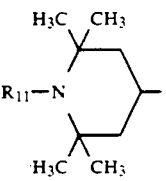
(II)

where $R_{11}$ is hydrogen, $C_1$–$C_8$alkyl, O, OH, NO, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or trisubstituted on the phenyl by $C_1$–$C_4$alkyl, or is $C_1$–$C_8$acyl and $R_9$ and $R_{10}$ which can be identical or different are as defined above for $R_8$ or are $C_2$–$C_4$alkyl substituted in the 2-, 3- or 4-position by $C_1$–$C_8$alkoxy or by di-($C_1$–$C_4$alkyl)-amino, or

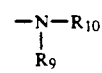

is a 5- to 7-membered heterocyclic group, $R_2$ and $R_5$ which can be identical or different are hydrogen, $C_1$–$C_{18}$alkyl, $C_5$–$C_{12}$cycloalkyl which is unsubstituted or mono-, di- or trisubstituted by $C_1$–$C_4$alkyl, $C_7$–$C_9$-phenylalkyl which is unsubstituted or mono-, di- or trisubstituted on the phenyl by $C_1$–$C_4$alkyl, or are a group of the formula (II) with the exception of this last definition for $R_5$ if both m and n are zero, $R_3$ and $R_4$ which can be identical or different are $C_2$–$C_6$alkylene, $R_7$ is one of the groups of the formulae (IIIa)–(IIIc), $$-A_1-R_{12}-A_2-,\quad\text{(IIIa)}$$

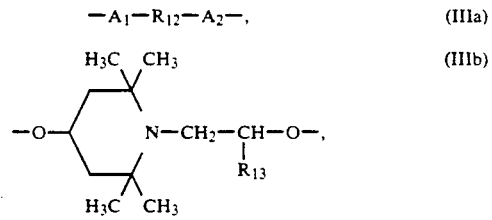

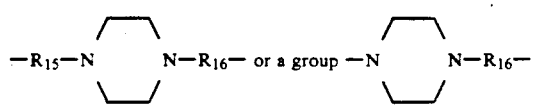

in which $A_1$ and $A_2$ which can be identical or different are $-O-$ or $>N-R_{14}$ being as defined above for $R_2$, $R_{12}$ is $C_2$–$C_{12}$alkylene, $C_4$–$C_{12}$alkylene interrupted by 1, 2 or 3 oxygen atoms or by a group $>N-CH_3$, cyclohexylene, cyclohexylenedimethylene, methylenedicyclohexylene, isopropylidenedicyclohexylene, phenylene, isopropylidenediphenylene or xylylene, or $R_{12}$ or $A_1R_{12}$ are, respectively, a group where $R_{15}$ and $R_{16}$ which
can be identical or different are $C_2$–$C_6$alkylene, $R_{13}$ is hydrogen or $C_1$–$C_8$alkyl, $A_3$ is a direct bond or $CH_2$ and r is zero, 1, 2 or 3, p is a number from 1 to 50 provided that p is different from 1 when n is zero, X is as defined above for $R_1$ or is Cl, ONa, OK or a group of the formula (IVa) or (IVb)

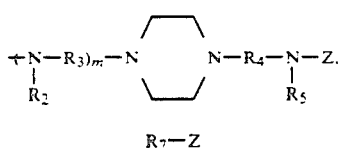

(IVa)

(IVb)

where m, $R_2$, $R_3$, $R_4$, $R_5$ and $R_7$ are as defined above, and Z is hydrogen, methyl, allyl, benzyl, acetyl or ($C_1$-$C_4$alkoxy)-carbonyl, Y is as defined above for Z or is a group of the formula (V)

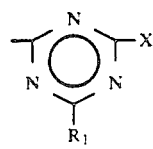

(V)

with $R_1$ and X as defined above.

In the compounds of the formula (I), it is a condition that at least one group of the formula (II) is present in each recurring unit.

Examples of $C_1$-$C_8$alkyl $R_{11}$ and $R_{13}$ are methyl, ethyl, propyl, butyl, isobutyl, pentyl, hexyl, heptyl and octyl. $C_1$-$C_4$Alkyl is preferred.

Examples of $C_1$-$C_{18}$alkyl are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. $C_1$-$C_{12}$Alkyl is preferred.

Representative examples of $C_2$-$C_4$alkyl $R_9$ and $R_{10}$ substituted by $C_1$-$C_8$alkoxy in the 2-, 3- or 4-position are 2-methoxyethyl, 2ethyoxyethyl, 3-methoxypropyl, 3-ethoxypropyl, 3-butoxypropyl, 3-octoxypropyl and 4-methoxybutyl. 3-Methoxypropyl and 3-ethoxypropyl are preferred.

Representative examples of $C_2$-$C_4$alkyl $R_9$ and $R_{10}$ substituted by di-($C_1$-$C_4$alkyl)-amino in the 2-, 3- or 4-position are 2-dimethylaminoethyl, 2-diethylaminoethyl, 3-dimethylaminopropyl, 3-diethylaminopropyl, 3-dibutylaminopropyl and 4-diethylaminobutyl. 3-Dimethylaminopropyl and 3-diethylaminopropyl are preferred.

Examples of alkoxy having up to 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$Alkoxy and in particular heptoxy and octoxy are preferred for $R_{11}$.

Representative examples of $C_5$-$C_{12}$cycloalkoxy $R_{11}$ are cyclopentoxy, cyclohexoxy, cycloheptoxy, cyclooctoxy, cyclodecyloxy and cyclododecyloxy. Cyclopentoxy and cyclohexoxy are preferred.

Examples of $C_5$-$C_{12}$cycloalkyl $R_2$, $R_5$, $R_8$, $R_9$, $R_{10}$ and $R_{14}$ which are unsubstituted or mono-, di- or trisubstituted by $C_1$-$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl is preferred.

Examples of alkenyl containing up to 18 carbon atoms areallyl, 2-methylallyl, butenyl, pentenyl, hexenyl, undecenyl and oleyl. Alkenyl in which the carbon atom in the 1-position is saturated is preferred; allyl is particularly preferred.

Examples of substituted phenyl are methylphenyl, dimethylphenyl, trimethylphenyl, t-butylphenyl, di-t-butylphenyl, methoxyphenyl and ethoxyphenyl.

Examples of $C_7$-$C_9$phenylalkyl $R_2$, $R_5$, $R_8$, $R_9$, $R_{10}$, $R_{11}$ and $R_{14}$ which are unsubstituted or mono-, di- or trisubstituted on the phenyl by $C_1$-$C_4$alkyl are benzyl, methylbenzyl, dimethylbenzyl, t-butylbenzyl and 2-phenylethyl. Benzyl is preferred.

Acyl $R_{11}$ containing up to 8 carbon atoms can be an aliphatic or aromatic group. Representative examples are formyl, acetyl, propionyl, butyryl, pentanoyl, hexanoyl, octanoyl, benzoyl, acryloyl or crotonoyl. $C_1$-$C_8$Alkanoyl, $C_3$-$C_8$alkenoyl and benzoyl are preferred. Acetyl is particularly preferred.

A 5- to 7-membered heterocyclic group

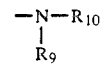

can contain a further heteroatom, for example nitrogen or oxygen; representative examples are 1-pyrrlidyl, 1-piperidyl, 4-morpholinyl, 4-methyl-1-piperazinyl and 1-hexahydroazepinyl. 4-Morpholinyl is preferred.

Examples of alkylene containing up to 12 carbon atoms are ethylene, propylene, trimethylene, tetramethylene, pentamethylene, 2,2-dimethyltrimethylene, hexamethylene, trimethylhexamethylene, octamethylene, decamethylene and dodecamethylene.

Representative examples of $C_4$-$C_{12}$alkylene $R_{12}$ interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl and 3,6,9-trioxaundecane-1,11-diyl.

Representative examples of $C_4$-$C_{12}$alkylene $R_{12}$ interrupted by a group >N-CH$_3$ are 3-methyl3-azapentane-1,5-diyl and 4-methyl-4-azaheptane-1,7-diyl.

Representative examples of ($C_1$-$C_4$alkoxy)-carbonyl are methoxycarbonyl, ethoxycarbonyl, propoxycarbonyl and butoxycarbonyl.

$R_{11}$ is preferably hydrogen, $C_1$-$C_4$alkyl, OH, $C_6$-$C_{12}$alkoxy, $C_5$-$C_8$cycloalkoxy, allyl, benzyl or acetyl, in particular hydrogen or methyl.

Those compounds of the formula (I) are preferred in which m is zero or 1, n is zero, 1, 2 or 3, $R_1$ and $R_6$ which can be identical or different are a group —$OR_8$,

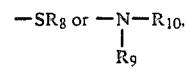

$R_8$ is $C_1$-$C_{12}$alkyl, $C_5$-$C_8$cycloalkyl, $C_3$-$C_{12}$alkenyl, benzyl, phenyl or a group of the formula (II), $R_9$ and $R_{10}$ which can be identical or different are as defined above for $R_8$ or are hydrogen or $C_2$-$C_3$alkyl substituted in the 2- or 3-position by $C_1$-$C_4$alkoxy or by di-($C_1$-$C_4$alkyl)-amino, or the group

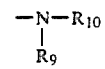

is 1-pyrrolidyl, 1-piperidyl, 4-morpholinyl, 4-methyl-1-piperazinyl or 1-hexahydroazepinyl, $R_2$ and $R_5$ which can be identical or different are hydrogen, $C_1-C_{12}$alkyl, $C_5-C_8$cycloalkyl, benzyl or a group of the formula (II) with the exception of this last definition for $R_5$ if both m and n are zero, $R_3$ and $R_4$ which can be identical or different are $C_2-C_6$alkylene, $R_7$ is one of the groups of the formulae (IIIa)-(IIIc) in which $A_1$ and $A_2$ which can be identical or different are —O— or >N—$R_{14}$ with $R_{14}$ being as defined above for $R_2$, $R_{12}$ is $C_2-C_{10}$alkylene, $C_4-C_{10}$alkylene interrupted by 1, 2 or 3 oxygen atoms or by a group >N—$CH_3$, cyclohexylene, cyclohexylenedimethylene, methylenedicyclohexylene, isopropylidenedicyclohexylene, isopropylidenediphenylene or xylylene, or $R_{12}$ or $A_1R_{12}$ are, respectively,

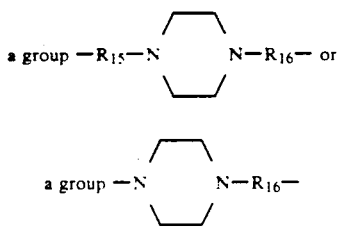

where $R_{15}$ and $R_{16}$ which can be identical or different are $C_2-C_6$alkylene, $R_{13}$ is hydrogen or $C_1-C_4$alkyl, $A_3$ is a direct bond or $CH_2$, r is zero, 1, 2 or 3, p is a number from 1 to 30 provided that p is different from 1 when n is zero, X is as defined above for $R_1$ or is Cl, ONa, OK or a group of the formula (IVa) or (IVb), Z and Y are hydrogen, methyl, allyl, benzyl, acetyl or ($C_1-C_4$alkoxy)-carbonyl, or Y is also a group of the formula (V); provided that the recurring unit of the formula (I) contains a group of the formula (II).

Those compounds of the formula (I) are particularly preferred in which m is zero or 1, n is zero, 1 or 2, $R_1$ and $R_6$ which can be identical or different are a group —$OR_8$, —$SR_8$ or

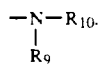

$R_8$ is $C_1-C_{12}$alkyl, cyclohexyl which is unsubstituted or mono-, di- or tri-substituted by $C_1-C_4$alkyl, allyl or undecenyl, benzyl, phenyl or a group of the formula (II), $R_9$ and $R_{10}$ which can be identical or different are as defined above for $R_8$ or are hydrogen or $C_2-C_3$alkyl substituted in the 2- or 3-position by $C_1-C_4$alkoxy, by dimethylamino or by diethylamino, or the group,

is 4-morpholinyl, $R_2$ and $R_5$ which can be identical or different are hydrogen, $C_1-C_{12}$alkyl, cyclohexyl which is unsubstituted or mono-, di- or tri-substituted by $C_1-C_4$alkyl, benzyl or a group of the formula (II) with the exception of this last definition for $R_5$ if both m and n are zero, $R_3$ and $R_4$ which can be identical or different are $C_2-C_4$alkylene, $R_7$ is one of the groups (IIIa)-(IIIc) in which $A_1$ and $A_2$ which can be identical or different are —O— or >N—$R_{14}$ with $R_{14}$ being as defined for $R_2$, $R_{12}$ is $C_2-C_8$alkylene, $C_4-C_{10}$alkylene interrupted by 1 or 2 oxygen atoms, cyclohexylenedimethylene, methylenedicyclohexylene, isopropylidenedicyclohexylene, isopropylidenediphenylene or xylylene, or $R_{12}$ or $A_1R_{12}$ are, respectively,

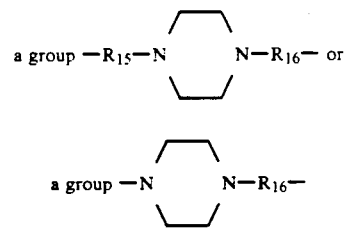

where $R_{15}$ and $R_{16}$ which can be identical or different are $C_2-C_4$alkylene, $R_{13}$ is hydrogen or methyl, $A_3$ is a direct bond or $CH_2$, r is zero, 1, 2 or 3, p is a number from 2 to 20, X is as defined above for $R_1$ or is ONa, OK or a group of the formula (IVa) or (IVb), Z and Y are hydrogen, methyl, allyl, benzyl, acetyl or ($C_1-C_2$alkoxy)-carbonyl or Y is also a group of the formula (V); provided that the recurring unit of the formula (I) contains a group of the formula (II).

Those compounds of the formula (I) are of special interest in which m is zero or 1, n is zero, 1 or 2, $R_1$ and $R_6$ which can be identical or different are

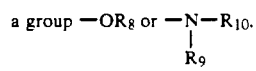

$R_8$ is $C_1-C_8$alkyl, cyclohexyl, allyl, phenyl or a group of the formula (II), $R_9$ and $R_{10}$ which can be identical or different are hydrogen, $C_1-C_8$alkyl, cyclohexyl, allyl, benzyl, a group of the formula (II) or $C_2-C_3$alkyl substituted in the 2- or 3-position by methoxy, by ethoxy, by dimethylamino or by diethylamino, or the group

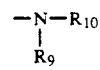

is 4-morpholinyl, $R_2$ and $R_5$ which can be identical or different are hydrogen, $C_1-C_8$alkyl, cyclohexyl, benzyl or a group of the formula (II) with the exception of this last definition for $R_5$ if both m and n are zero, $R_3$ and $R_4$ which can be identical or different are $C_2-C_3$alkylene, $R_7$ is one of the groups of the formulae (IIIa)-(IIIc) in which $A_1$ and $A_2$ which can be identical or different are —O— or >N—$R_{14}$ with $R_{14}$ being as defined above for $R_2$, $R_{12}$ is $C_2-C_6$alkylene, $C_4-C_{10}$alkylene interrupted by 1 or 2 oxygen atoms, cyclohexylenedimethylene, methylenedicyclohexylene or isopropylidenediphenylene, or $R_{12}$ or $A_1R_{12}$ are, respectively,

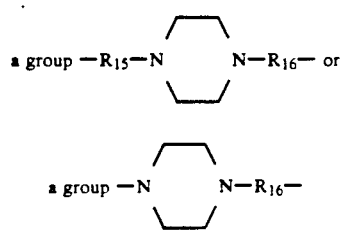

where $R_{15}$ and $R_{16}$ which can be identical or different are $C_2-C_3$ alkylene, $R_{13}$ is hydrogen or methyl, $A_3$ is a direct bond, p is a number from 2 to 15, X is ONa, OK or a group of the formula (IVa) or (IVb), Z and Y are hydrogen, methyl, acetyl or ($C_1$-$C_2$alkoxy)-carbonyl; provided that the recurring unit of the formula (I) contains a group of the formula (II).

Those compounds of the formula (I) are of particular interest in which m and n which can be identical or different are zero or 1, $R_1$ and $R_6$ are

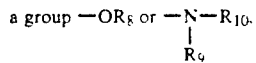

$R_8$ is $C_1$-$C_4$alkyl, 2,2,6,6-tetramethyl-4-piperidyl or 1,2,2,6,6-pentamethyl-4-piperidyl, $R_9$ and $R_{10}$ which can be identical or different are $C_1$-$C_8$alkyl, cyclohexyl, 2,2,6,6-tetramethyl-4-piperidyl or 1,2,2,6,6-pentamethyl-4-piperidyl, or $R_9$ is also hydrogen, or the group

is 4-morpholinyl, $R_2$ and $R_5$ are hydrogen, methyl, 2,2,6,6-tetramethyl-4-piperidyl or 1,2,2,6,6-pentamethyl-4-piperidyl with the exception of these last two definitions for $R_5$ if both m and n are zero, $R_3$ and $R_4$ which can be identical or different are $C_2$-$C_3$alkylene, $R_7$ is

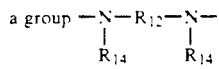

or 1,4-piperazinediyl, $R_{12}$ is $C_2$-$C_6$alkylene, $C_4$-$C_{10}$alkylene interrupted by 1 or 2 oxygen atoms, cyclohexylenedimethylene or methylenedicyclohexylene, $R_{14}$ is as defined above for $R_2$, p is a number from 2 to 10, X is a group of the formula (IVa) or (IVb), and Z and Y are hydrogen or methyl; provided that the recurring unit of the formula (I) contains 2,2,6,6-tetramethyl-4-piperidyl or 1,2,2,6,6-pentamethyl-4-piperidyl.

The compounds of the formula (I) can be prepared by processes known per se, for example as described in U.S. Pat. Nos. 4,086,204 and 4,459,395, by reacting dichlorotriazines of the formulae (VIa) and (VIb)

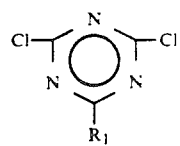

(VIa)

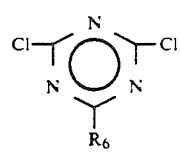

(VIb)

with the compounds of the formulae (VIIa) and (VIIb)

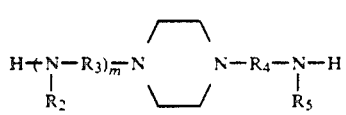

(VIIa)

and

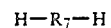

H—$R_7$—H        (VIIb)

in the appropriate molar ratios.

The reactions are preferably carried out in an aromatic hydrocarbon solvent, for example toluene, xylene or trimethylbenzene, operating at temperatures of e.g. 40° to 200° C., preferably 50° to 180° C.

The hydrochloric acid set free in the reactions is preferably neutralized with an inorganic base, for example sodium or potassium hydroxide or carbonate, in a quantity at least equivalent to the acid set free.

The dichlorotriazines of the formulae (VIa) and (VIb) are prepared e.g. by reacting cyanuric chloride with compounds $R_1$-H and $R_6$-H in an equimolar ratio.

If $R_1$=$R_6$, the dichlorotriazine used for the reaction is conveniently prepared in a single reactor and subsequently reacted with the compounds of the formulae (VIIa) and (VIIb) without previous isolation from the reaction mixture.

If $R_{11}$, Y and Z are $CH_3$, the compounds of the formula (I) are preferably prepared by reacting the corresponding compounds, in which $R_{11}$, Y and Z are hydrogen, with formaldehyde and formic acid or with formaldehyde and hydrogen in the presence of a hydrogenation catalyst such as palladium or platinum.

Depending on the type and molar amounts of the reagents used for the preparation of the instant compounds, the product obtained may be a mixture of compounds of the formula (I) having different terminal groups X and Y. This mixture can be separated, if desired, with the aid of for example chromatographic methods, in particular high-pressure liquid chromatography (HPLC).

A preferred embodiment of the instant invention also relates to compounds of the formula (I) obtainable by reacting dichlorotriazines of the formula (VIa) and (VIb) with compounds of the formulae (VIIa) and (VIIb).

As mentioned at the outset, the compounds of the formula (I) are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Statistical or alternating copolymers of α-olefines with carbon monoxide.

3b. Hydrocarbon resins (for example $C_5$–$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from copolymers of styrene and other polymers, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene; styrene on polybutadiene; styrene on polybutadiene-styrene or polybutadiene-acrylonitrile; styrene and acrylonitrile (or methacrylonitrile) on polybutadiene; styrene and maleic anhydride or maleimide or polybutadiene; styrene, acrylonitrile and maleic anhydride or maleimide on polybutadiene; styrene, acrylonitrile and methyl methacrylate on polybutadiene; styrene and alkyl acrylates or methacrylates on polybutadiene; styrene and acrylonitrile on ethylene/propylene/diene terpolymers; styrene and acrylonitrile on polyacrylates or polymethacrylates; styrene and acrylonitrile on acrylate/butadiene copolymers, as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, such as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers. 8. Polymers which are derived from α,β-unsaturated acids and derivatives thereof, such as polyacrylates and polymethacrylates, polyacrylamide and polyacrylonitrile. 9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers. 10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above. 11. Homopolymers and copolymers of cyclic ethers, such as polyalkylene glycols, polyethylene oxide, polypropylene oxide or copolymers thereof with bis-glycidyl ethers. 12. Polyacetals, such as polyoxymethylene and polyoxymethylenes which contain ethylene oxide as a comonomer; polyacetals modified with thermoplastic polyurethanes, acrylates or MBS. 13. Polyphenylene oxides and sulfides, and mixtures of polyphenylene oxides with polystyrene and polyamides. 14. Polyurethanes which are derived from polyethers, polyesters or polybutadiene with terminal hydroxyl groups on the one hand and aliphatic or aromatic polyisocyanates on the other hand, as well as precursors thereof (polyisocyanates, polyols or prepolymers). 15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethyeneterephthalamide or poly-m-phenylene-isophthalamide. Further, copolymers of the aforementioned polyamides with polyolefins, olefin copolymers, ionomers or chemically bonded or grafted elastomers; or with polyethers, as, for instance, with polyethylene glycols, polypropylene glycols or polytetramethylene glycols. Polyamides or copolyamides modified with EPDM or ABS. Polyamides condensed during processing (RIM-polyamide systems). 16. Polyureas, polyimides and polyamide-imides. 17. Polyesters which are derived from dicarboxylic acids and diols and/or from hydroxy carboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoate as well as block copolyether-esters derived from polyethers having hydroxyl end groups. 18. Polycarbonates and polyester-carbonates. 19. Polysulfones, polyethersulfones and polyether-ketones. 20. Crosslinked polymers which are derived from aldehydes on the one hand and phenols, ureas and melamines on the other hand, such as phenol/formaldehyde resins, urea/formaldehyde resins and melamine/formaldehyde resins. 21. Drying and non-drying alkyd resins. 22. Unsaturated polyester resins which are derived from copolyesters of saturated and unsaturated dicarboxylic acids with polyhydric alcohols and vinyl compounds as crosslinking agents, and also halogen-containing modifications thereof of low flammability. 23. Thermosetting acrylic resins, derived from substituted acrylic esters, such as epoxy-acrylates, urethane-acrylates or polyester-acrylates. 24. Alkyd resins, polyester resins or acrylate resins in admixture with melamine resins, urea resins, polyisocyanates or epoxide resins as crosslinking agents. 25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of the polymers mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratio, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

In general, the compounds of the formula (I) can be added to the polymeric materials before, during or after the polymerization or crosslinking of the said materials.

The compounds of formula (I) can be incorporated into the material to be stabilized in a pure form or encapsulated in waxes, oils or polymers.

The materials stabilized with the products of the formula (I) can be used for the production of mouldings, films, tapes, monofilaments, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in a mixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxamide.

1.9. Esters of β-(3,5-dicyclohexyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.10. Amides of β-(3,5-di-tert-butyl-4-hydroxyphenyl)-propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example the 5'-methyl, 3'-, 5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy-3',5'-di-tert-amyl and 3',5'-bis-(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2', 4'-trihydroxy and 2'-hydroxy-4,4'-dimethoxy derivatives.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl)sebacate, bis(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrolotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid diamides, for example, 4,4'-dioctyloxyoxanilide, 2,2'-dioctyloxy-5,5'-di-tert-butylyoxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

4. bis. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate, bis(1-hydroxy-2,2,6,6-tetramethyl-4-piperidyl)sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

The compounds of formula (I) can also be used as stabilizers, especially light stabilizers, for almost all materials known in the art of photographic reproduction and other reproduction techniques as e.g. described in Research Disclosure 1990, 31429 (pages 474 to 480).

The following examples are reported as illustrating the present invention, but without restricting it. The compounds of Examples 2, 6 and 7 relate to a particularly preferred embodiment of the instant invention.

EXAMPLE 1

17.42 g (0.2 mol) of morpholine are added to a solution of 36.90 g (0.2 mol) of cyanuric chloride in 300 ml of xylene, maintaining the temperature at 10° C. After the end of the addition, the mixture is stirred for a further ½ hour at ambient temperature, and a solution of 8.8 g (0.22 mol) of sodium hydroxide in 30 ml of water is then added. After stirring for ½ hour, the aqueous phase is separated off, and 105.34 g (0.22 mol) of N,N'-bis-[3-(2,2,6,6-tetramethyl-4-piperidylamino)-propyl]-piperazine are added to the xylene solution; the mixture is heated at 80° C. for 2 hours, 32.0 g (0.8 mol) of sodium hydroxide are added and the mixture is heated under reflux for 16 hours, the water of reaction being removed azeotropically. The mixture is then cooled to about 60° C. and filtered, and the filtrate is washed with water.

The solution is then dried over anhydrous sodium sulfate and evaporated in vacuo (2 mbar), giving a compound of melting point 118°–123° C. and $\overline{M}n=2,200$, containing recurring units of the formula

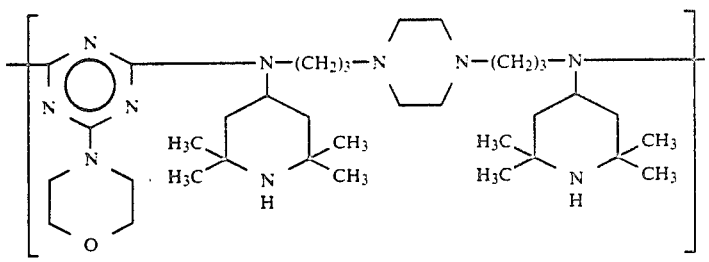

EXAMPLES 2-5

Following the procedure described in Example 1 and choosing the respective reagents in the appropriate molar ratios, the following compounds containing recurring units of the formula

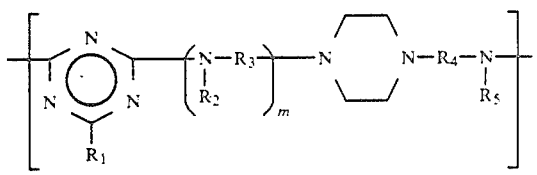

are prepared.

| Example | $R_1$ | m | $R_2$ | $R_3$ | $R_4$ | $R_5$ | m.p. (°C.) ($\overline{M}n$) |
|---|---|---|---|---|---|---|---|
| 2 | —NH—C(CH₃)₂—CH₂—C(CH₃)₂—CH₃ | 1 | 2,2,6,6-tetramethylpiperidinyl | —(CH₂)₃— | —(CH₂)₃— | 2,2,6,6-tetramethylpiperidinyl | 152–157 (2800) |
| 3 | 2,2,6,6-tetramethyl-4-(HN-)piperidyl-N— | 1 | 2,2,6,6-tetramethylpiperidinyl | —(CH₂)₃— | —(CH₂)₃— | 2,2,6,6-tetramethylpiperidinyl | 201–207 (3000) |
| 4 | 2,2,6,6-tetramethyl-4-(HN-)piperidyl-N— | 1 | —H | —(CH₂)₃— | —(CH₂)₃— | —H | 167–173 (2500) |

| Example | $R_1$ | m | $R_2$ | $R_3$ | $R_4$ | $R_5$ | m.p. (°C.) (Mn) |
|---|---|---|---|---|---|---|---|
| 5 | 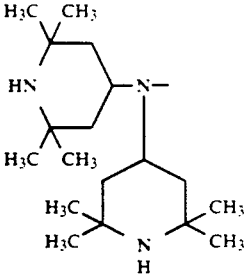 | 0 | / | / | $-(CH_2)_2-$ | $-H$ | 231–235 (2000) |

EXAMPLE 6

A solution of 39.47 g (0.1 mol) of N,N'-bis-(2,2,6,6-tetramethyl-4-piperidyl)-1,6-hexanediamine in 150 ml of xylene is added to a solution of 72.06 g (0.2 mol) of 2,4-dichloro-6-[N-(2,2,6,6-tetramethyl-4-piperidyl)-butylamino]-1,3,5-triazine in 400 ml of xylene. The mixture is heated at 60° C. for 2 hours, and a solution of 62.24 g (0.13 mol) of N,N'-bis[3-(2,2,6,6-tetramethyl-4-piperidylamino)propyl]-piperazine in 100 ml of xylene is then added, always at 60° C. The mixture is heated under reflux for 4 hours, then 32.0 g (0.8 mol) of sodium hydroxide are added and the mixture is heated under reflux for 16 hours, the water of reaction being eliminated azeotropically. The mixture is then cooled to 60° C. and filtered, and the filtrate is washed with water. The solution is then dried over anhydrous sodium sulfate and evaporated in vacuo, giving a compound of melting point 171°–176° C. and $\overline{Mn}=3,200$, containing recurring units of the formula

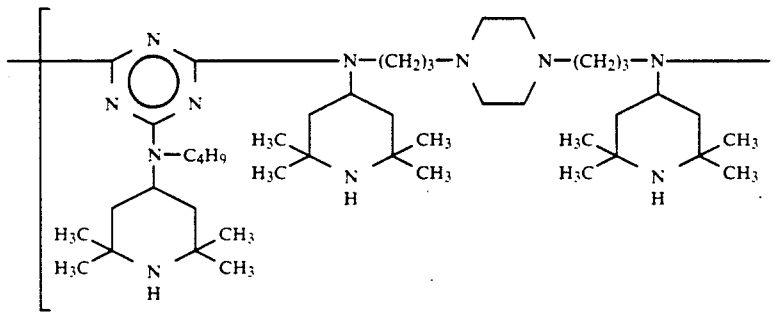

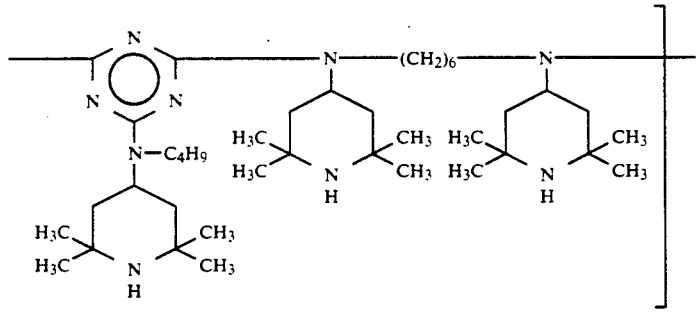

EXAMPLES 7–10

Following the procedure described in Example 6 and using the respective reagents in the appropriate molar ratios, the following compounds containing recurring units of the formula

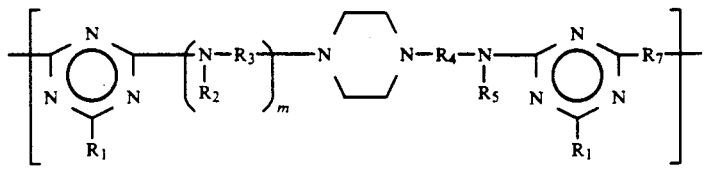

are prepared.

| Example | R₁ | m | R₂ | R₃ | R₄ | R₅ | R₇ | M.p. (°C.) (Mn) |
|---------|----|----|----|----|----|----|----|------|
| 7 | —NH—C(CH₃)₂—CH₂—C(CH₃)₂—CH₃ | 1 | 2,2,6,6-tetramethylpiperidin-4-yl | —(CH₂)₃— | —(CH₂)₃— | 2,2,6,6-tetramethylpiperidin-4-yl | —N[2,2,6,6-tetramethylpiperidin-4-yl]—(CH₂)₆—N(H)[2,2,6,6-tetramethylpiperidin-4-yl] | 119–123 (2450) |
| 8 | —N(2,2,6,6-tetramethylpiperidin-4-yl)— | 1 | —H | —(CH₂)₃— | —(CH₂)₃— | —H | —N(H)—(CH₂)₃—O—(CH₂)₂—O—(CH₂)₃—N(H)— | 122–125 (2600) |
| 9 | —N—C₄H₉ (2,2,6,6-tetramethylpiperidin-4-yl) | 1 | —H | —(CH₂)₃— | —(CH₂)₃— | —H | —N[2,2,6,6-tetramethylpiperidin-4-yl]—(CH₂)₆—N(H)[2,2,6,6-tetramethylpiperidin-4-yl] | 129–134 (3300) |
| 10 | —N(2,2,6,6-tetramethylpiperidin-4-yl)— | 0 | / | / | —(CH₂)₂— | —H | —N(H)—(CH₂)₃—O—(CH₂)₂—O—(CH₂)₃—N(H)— | 206–211 (3000) |

EXAMPLE 11

A solution containing 3.96 g (0.13 mol) of 37% formaldehyde and 5.1 g (0.127 mol) of formic acid is added within one hour to a solution containing 23.3 g of the compound from Example 3 in 60 ml of xylene, heated to 110° C. After the end of the addition, the mixture is kept for 2 hours at 110° C. and, after cooling to ambient temperature, a solution of 6.1 g (0.15 mol) of sodium hydroxide in 30 ml of water is added and the mixture is stirred for ½ hour. The organic phase is washed with water, dried over anhydrous sodium sulfate and evaporated in vacuo giving a compound of melting point 222°-226° C. and $\overline{Mn}=3,300$, containing recurring units of the formula

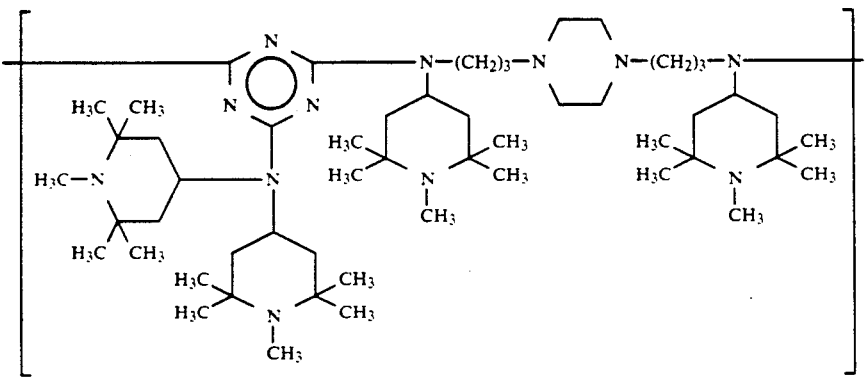

The number average molecular weight indicated in the above examples is determined according to the method described in EP-A-255,990, page 18, line 54 to page 19, line 15.

EXAMPLE 12

2.5 g of each of the products indicated in Table 1, 1.0 g of tris-(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°-230° C. to give polymer granules which are then converted into fibres, using a pilot-type apparatus (Leonard, Sumirago (VA), Italy) and operating under the following conditions:

| | |
|---|---|
| extruder temperature | 220-230° C. |
| head temperature | 255-260° C. |
| stretch ratio | 1:3.5 |
| count | 11 dtex per filament |

The fibres thus prepared are exposed, mounted on a white card, in a model 65 WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated. Fibres prepared under the same conditions as indicated above, but without addition of the compounds of the invention, are exposed for comparison.

The results obtained are shown in Table 1:

TABLE 1

| Stabilizer | $T_{50}$(hours) |
|---|---|
| none | 150 |
| Compound from Example 1 | 1150 |
| Compound from Example 2 | 1100 |
| Compound from Example 3 | 1300 |
| Compound from Example 5 | 1230 |
| Compound from Example 6 | 1240 |
| Compound from Example 7 | 1400 |
| Compound from Example 9 | 1220 |

What is claimed is:
1. A compound of the formula (I)

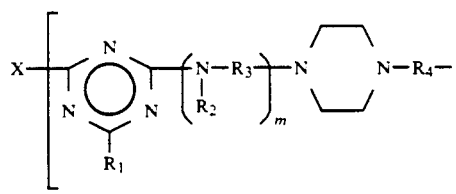

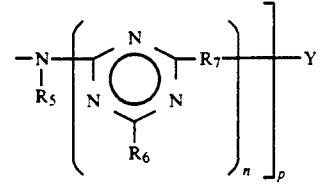

in which m is zero or 1, n is zero, 1, 2, 3 or 4, $R_1$ and $R_6$ which can be identical or different are a group —$OR_8$, —$SR_8$ or

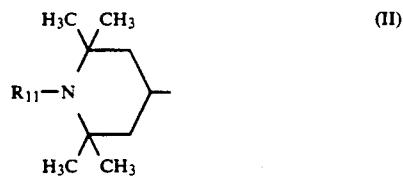

in which $R_8$ is hydrogen, $C_1$-$C_{18}$alkyl, $C_5$-$C_{12}$cycloalkyl which is unsubstituted or mono-, di- or trisubstituted by $C_1$-$C_4$alkyl, $C_3$-$C_{18}$alkenyl, $C_7$-$C_9$phenylalkyl which is unsubstituted or mono-, di- or trisubstituted on the phenyl by $C_1$-$C_4$alkyl, phenyl which is unsubstituted or mono-, di- or tri-substituted by $C_1$-$C_4$alkyl or by $C_1$-$C_4$alkoxy, or a group of the formula (II)

where $R_{11}$ is hydrogen, $C_1$-$C_8$alkyl, O, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di-or trisubstituted on the phenyl by $C_1$-$C_4$alkyl, or is $C_1$-$C_8$acyl and $R_9$ and $R_{10}$ which can be identical or different are as defined above for $R_8$ or are $C_2$-$C_4$alkyl substituted in the 2-, 3-or 4-position by $C_1$-$C_8$alkoxy or by di-($C_1$-$C_4$alkyl)-amino,

is a 5- to 7-membered heterocyclic group, $R_2$ and $R_5$ which can be identical or different are hydrogen, $C_1$-$C_{18}$alkyl, $C_5$-$C_{12}$cycloalkyl which is unsubstituted or mono-, di- or trisubstituted by $C_1$-$C_4$alkyl, $C_7$-$C_9$-phenylalkyl which is unsubstituted or mono-, di- or trisubstituted on the phenyl by $C_1$-$C_4$alkyl, or are a group of the formula (II) with the exception of this last definition for $R_5$ if both m and n are zero, $R_3$ and $R_4$ which can be identical or different are $C_2$-$C_6$alkylene, $R_7$ is one of the groups of the formulae (IIIa)-(IIIc),

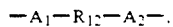

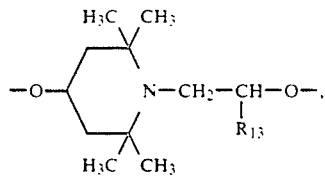

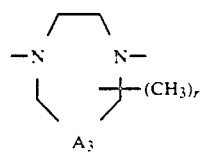

in which $A_1$ and $A_2$ which can be identical or different are —O— or >N—$R_{14}$ with $R_{14}$ being as defined above for $R_2$, $R_{12}$ is $C_2$-$C_{12}$alkylene, $C_4$-$C_{12}$alkylene interrupted by 1, 2 or 3 oxygen atoms or by a group >N—$CH_3$, cyclohexylene, cyclohexylenedimethylene, methylenedicyclohexylene, isopropylidenedicyclohexylene, phenylene, isopropylidenediphenylene or xylylene, or $R_{12}$ or $A_1R_{12}$ are, respectively, a group

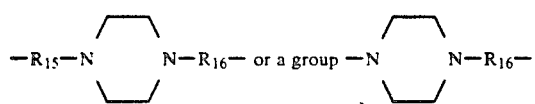

where $R_{15}$ and $R_{16}$ which can be identical or different are $C_2$-$C_6$alkylene, $R_{13}$ is hydrogen or $C_1$-$C_8$alkyl, $A_3$ is a direct bond or $CH_2$ and r is zero, 1, 2 or 3, p is a number from 1 to 50 provided that p is different from 1 when n is zero, X is as defined above for $R_1$ or is Cl, ONa, OK or a group of the formula (IVa) or (IVb)

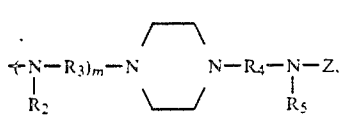

where m, $R_2$, $R_3$, $R_4$, $R_5$ and $R_7$ are as defined above, and Z is hydrogen, methyl, allyl, benzyl, acetyl or ($C_1$-$C_4$alkoxy)-carbonyl, Y is as defined above for Z or is a group of the formula (V)

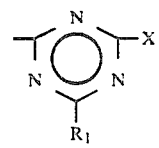

with $R_1$ and X as defined above; with the proviso that the recurring unit of the formula (I) contains a group of the formula (II).

2. A compound of the formula (I) according to claim 1, in which $R_{11}$ is hydrogen, $C_1$-$C_4$alkyl, OH, $C_6$-$C_{12}$alkoxy, $C_5$-$C_8$cycloalkoxy, allyl, benzyl or acetyl.

3. A compound of the formula (I) according to claim 1, in which m is zero or 1, n is zero, 1, 2 or 3, $R_1$ and $R_6$ which can be identical or different are a group —$OR_8$, —$SR_8$ or

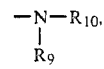

$R_8$ is $C_1$-$C_{12}$alkyl, $C_5$-$C_8$cycloalkyl, $C_3$-$C_{12}$alkenyl, benzyl, phenyl or a group of the formula (II), $R_9$ and $R_{10}$ which can be identical or different are as defined above for $R_8$ or are hydrogen or $C_2$-$C_3$alkyl substituted in the 2- or 3-position by $C_1$-$C_4$alkoxy or by di-($C_1$-$C_4$alkyl)-amino, or the group

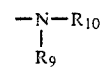

is 1-pyrrolidyl, 1-piperidyl, 4-morpholinyl, 4-methyl-1-piperazinyl or 1-hexahydroazepinyl, $R_2$ and $R_5$ which can be identical or different are hydrogen, $C_1$-$C_{12}$alkyl, $C_5$-$C_8$cycloalkyl, benzyl or a group of the formula (II) with the exception of this last definition for $R_5$ if both m and n are zero, $R_3$ and $R_4$ which can be identical or different are $C_2$-$C_6$alkylene, $R_7$ is one of the groups of the formulae (IIIa)-(IIIc) in which $A_1$ and $A_2$ which can be identical or different are —O— or >N—$R_{14}$ with $R_{14}$ being as defined above for $R_2$, $R_{12}$ is $C_2$-$C_{10}$alkylene, $C_4$-$C_{10}$alkylene interrupted by 1, 2 or 3 oxygen atoms or by a group >N—$CH_3$, cyclohexylene, cyclohexylenedimethylene, methylenedicyclohexylene, isopropylidenedicyclohexylene, isopropylidenediphenylene or xylylene, or $R_{12}$ or $A_1R_{12}$ are, respectively;

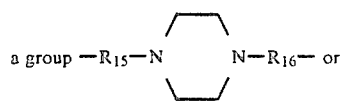

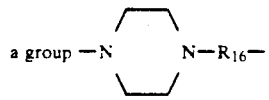

where $R_{15}$ and $R_{16}$ which can be identical or different are $C_2$-$C_6$alkylene, $R_{13}$ is hydrogen or $C_1$-$C_4$alkyl, $A_3$ is a direct bond or $CH_2$, r is zero, 1, 2 or 3, p is a number from 1 to 30 provided that p is different from 1 when n is zero, X is as defined above for $R_1$ or is Cl, ONa, OK or a group of the formula (IVa) or (IVb), Z and Y are hydrogen, methyl, allyl, benzyl, acetyl or ($C_1$-$C_4$alkoxy)-carbonyl, or Y is also a group of the formula (V); provided that the recurring unit of the formula (I) contains a group of the formula (II).

4. A compound of the formula (I) according to claim 1, in which m is zero or 1, n is zero, 1 or 2, $R_1$ and $R_6$ which can be identical or different are a group —$OR_8$, —$SR_8$ or

$R_8$ is $C_1$-$C_{12}$alkyl, cyclohexyl which is unsubstituted or mono-, di- or tri-substituted by $C_1$-$C_4$alkyl, allyl or undecenyl, benzyl, phenyl or a group of the formula (II), $R_9$ and $R_{10}$ which can be identical or different are as defined above for $R_8$ or are hydrogen or $C_2$-$C_3$alkyl substituted in the 2- or 3-position by $C_1$-$C_4$alkoxy, by dimethylamino or by diethylamino, or the group

is 4-morpholinyl, $R_2$ and $R_5$ which can be identical or different are hydrogen, $C_1$-$C_{12}$alkyl, cyclohexyl which is unsubstituted or mono-, di- or tri-substituted by $C_1$-$C_4$alkyl, benzyl or a group of the formula (II) with the exception of this last definition for $R_5$ if both m and n are zero, $R_3$ and $R_4$ which can be identical or different are $C_2$-$C_4$alkylene, $R_7$ is one of the groups (IIIa)-(IIIc) in which $A_1$ and $A_2$ which can be identical or different are —O— or >N—$R_{14}$ with $R_{14}$ being as defined for $R_2$, $R_{12}$ is $C_2$-$C_8$alkylene, $C_4$-$C_{10}$alkylene interrupted by 1 or 2 oxygen atoms, cyclohexylenedimethylene, methylenedicyclohexylene, isopropylidenedicyclohexylene, isopropylidenediphenylene or xylylene, or $R_{12}$ or $A_1R_{12}$ are, respectively, a group

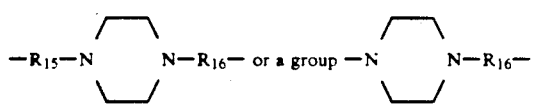

where $R_{15}$ and $R_{16}$ which can be identical or different are $C_2$-$C_4$alkylene, $R_{13}$ is hydrogen or methyl, $A_3$ is a direct bond or $CH_2$, r is zero, 1, 2 or 3, p is a number from 2 to 20, X is as defined above for $R_1$ or is ONa, OK or a group of the formula (IVa) or (IVb), Z and Y are hydrogen, methyl, allyl, benzyl, acetyl or ($C_1$-$C_2$alkoxy)-carbonyl or Y is also a group of the formula (V); provided that the recurring unit of the formula (I) contains a group of the formula (II).

5. A compound of the formula (I) according to claim 1, in which m is zero or 1, n is zero, 1 or 2, $R_1$ and $R_6$ which can be identical or different are a group —$OR_8$ or

$R_8$ is $C_1$-$C_8$alkyl, cyclohexyl, allyl, phenyl or a group of the formula (II), $R_9$ and $R_{10}$ which can be identical or different are hydrogen, $C_1$-$C_8$alkyl, cyclohexyl, allyl, benzyl, a group of the formula (II) or $C_2$-$C_3$alkyl substituted in the 2- or 3-position by methoxy, by ethoxy, by dimethylamino or by diethylamino, or the group

is 4-morpholinyl, $R_2$ and $R_5$ which can be identical or different are hydrogen, $C_1$-$C_8$alkyl, cyclohexyl, benzyl or a group of the formula (II) with the exception of this last definition for $R_5$ if both m and n are zero, $R_3$ and $R_4$ which can be identical or different are $C_2$-$C_3$alkylene, $R_7$ is one of the groups of the formulae (IIIa)-(IIIc) in which $A_1$ and $A_2$ which can be identical or different are —O— or >N—$R_{14}$ with $R_{14}$ being as defined above for $R_2$, $R_{12}$ is $C_2$-$C_6$alkylene, $C_4$-$C_{10}$alkylene interrupted by 1 or 2 oxygen atoms, cyclohexylenedimethylene, methylenedicyclohexylene or isopropylidenediphenylene, or $R_{12}$ or $A_1R_{12}$ are, respectively,

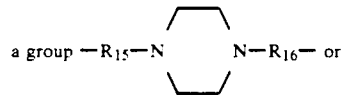

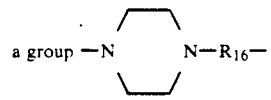

where $R_{15}$ and $R_{16}$ which can be identical or different are $C_2$-$C_3$alkylene, $R_{13}$ is hydrogen or methyl, $A_3$ is a direct bond, p is a number from 2 to 15, X is ONa, OK or a group of the formula (IVa) or (IVb), Z and Y are hydrogen, methyl, acetyl or ($C_1$-$C_2$alkoxy)-carbonyl; provided that the recurring unit of the formula (I) contains a group of the formula (II).

6. A compound of the formula (I) according to claim 1, in which m and n which can be identical or different are zero or 1, $R_1$ and $R_6$ are a group -$OR_8$ or

$R_8$ is $C_1$-$C_4$alkyl, 2,2,6,6-tetramethyl-4-piperidyl or 1,2,2,6,6-pentamethyl-4-piperidyl, $R_9$ and $R_{10}$ which can be identical or different are $C_1$-$C_8$alkyl, cyclohexyl, 2,2,6,6-tetramethyl-4-piperidyl or 1,2,2,6,6-pentamethyl-4-piperidyl, or $R_9$ is also hydrogen, or the group

is 4-morpholinyl, $R_2$ and $R_5$ are hydrogen, methyl, 2,2,6,6-tetramethyl-4-piperidyl or 1,2,2,6,6-pentamethyl-4-piperidyl with the exception of these last two definitions for $R_5$ if both m and n are zero, $R_3$ and $R_4$ which can be identical or different are $C_2$-$C_3$alkylene, $R_7$ is

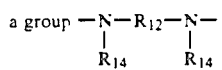

or 1,4-piperazinediyl, $R_{12}$ is $C_2$-$C_6$alkylene, $C_4$-$C_{10}$alkylene interrupted by 1 or 2 oxygen atoms, cyclohexylenedimethylene or methylenedicyclohexylene, $R_{14}$ is as defined above for $R_2$, p is a number from 2 to 10, X is a group of the formula (IVa) or (IVb), and Z and Y are hydrogen or methyl; provided that the recurring unit of the formula (I) contains 2,2,6,6-tetramethyl-4-piperidyl or 1,2,2,6,6-pentamethyl-4-piperidyl.

7. A compound of the formula (I) according to claim 1 with the recurring units of the formula

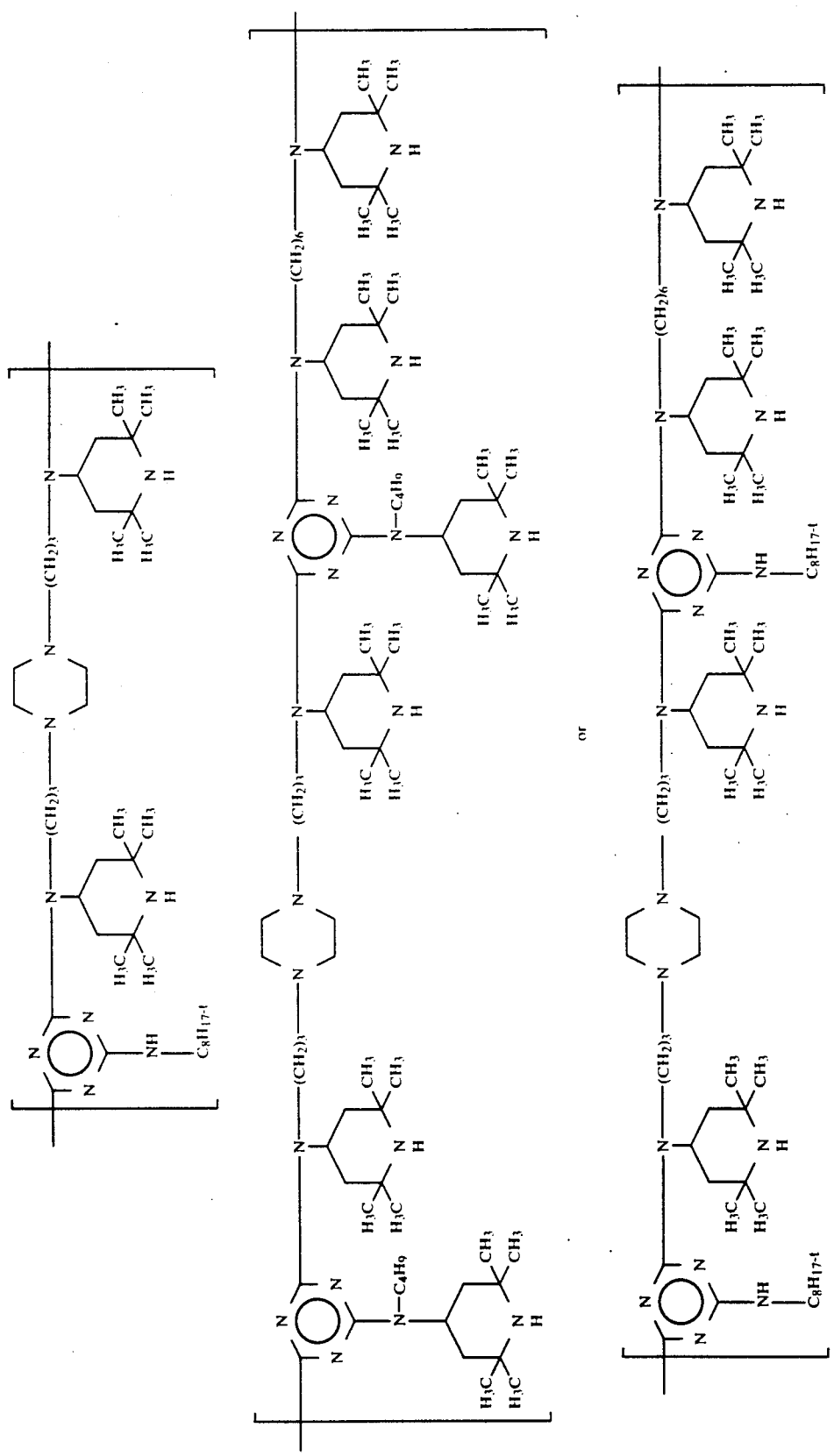

8. A composition which contains an organic material susceptible to degradation induced by light, heat and oxidation and an effective stabilizing amount of a compound of the formula (I) according to claim 1.

9. A composition according to claim 8, wherein the organic material is a synthetic polymer.

10. A composition according to claim 9, which contains other conventional additives for synthetic polymers, in addition to the compound of the formula (I).

11. A composition according to claim 8, wherein the organic material is a polyolefin.

12. A composition according to claim 8, wherein the organic material is polyethylene or polypropylene.

13. A method for stabilizing an organic material against degradation induced by light, heat or oxidation, which comprises incorporating into said material an effective stabilizing amount of a compound of the formula (I) according to claim 1.

* * * * *